(12) United States Patent
Song et al.

(10) Patent No.: US 10,613,050 B2
(45) Date of Patent: Apr. 7, 2020

(54) BIO SENSOR AND SENSING METHOD THEREOF

(71) Applicant: Samsung Electronics Co., Ltd., Suwon-si, Gyeonggi-do (KR)

(72) Inventors: Youn-joo Song, Seoul (KR); Seong-je Cho, Suwon-si (KR); Kwang-bok Kim, Incheon (KR); Young-jae Oh, Suwon-si (KR); Jae-geol Cho, Yongin-si (KR); Hyoung-seon Choi, Seoul (KR)

(73) Assignee: Samsung Electronics Co., Ltd., Suwon-si (JP)

( * ) Notice: Subject to any disclaimer, the term of this patent is extended or adjusted under 35 U.S.C. 154(b) by 209 days.

(21) Appl. No.: 15/341,524

(22) Filed: Nov. 2, 2016

(65) Prior Publication Data

US 2017/0122895 A1 May 4, 2017

(30) Foreign Application Priority Data

Nov. 3, 2015 (KR) .................. 10-2015-0154026

(51) Int. Cl.
*G01N 27/327* (2006.01)
*G01N 27/28* (2006.01)
*G01N 27/30* (2006.01)
*C12Q 1/00* (2006.01)

(52) U.S. Cl.
CPC ......... *G01N 27/3273* (2013.01); *C12Q 1/006* (2013.01)

(58) Field of Classification Search
CPC ...... G01N 27/48; G01N 27/26; G01N 27/327; G01N 27/3272; G01N 27/40; G01N 33/49; G01N 33/80; G01N 33/26; C12Q 1/00; C12Q 1/02; C12Q 1/006; C12Q 1/34; C12Q 1/54; A61B 5/05; A61B 5/14532; A61B 5/14535
See application file for complete search history.

(56) References Cited

U.S. PATENT DOCUMENTS

| | | | |
|---|---|---|---|
| 5,411,647 | A | 5/1995 | Johnson et al. |
| 9,008,745 | B2 | 4/2015 | Pushpala et al. |
| 2004/0084307 | A1 | 5/2004 | Kim et al. |
| 2006/0009691 | A1 | 1/2006 | Yeo et al. |
| 2007/0235347 | A1* | 10/2007 | Chatelier ............ C12Q 1/001 205/792 |
| 2007/0240986 | A1 | 10/2007 | Reymond et al. |

(Continued)

FOREIGN PATENT DOCUMENTS

| JP | 2005-017183 A | 1/2005 |
|---|---|---|
| JP | 3715910 B2 | 11/2005 |

(Continued)

*Primary Examiner* — Gurpreet Kaur
(74) *Attorney, Agent, or Firm* — Jefferson IP Law, LLP

(57) ABSTRACT

A bio sensor a method of sensing for the bio sensor are provided. The bio sensor includes an electrode array. The electrode array includes an enzyme electrode for measuring a target material, a power driver for providing a voltage to the electrode array, and a processor for controlling the power driver to alternately provide a negative voltage and a positive voltage to the electrode array, and for controlling the power driver to provide a measurement voltage for measuring the target material to the electrode array after the alternating voltage is provided.

13 Claims, 13 Drawing Sheets

(56) References Cited

U.S. PATENT DOCUMENTS

| | | | |
|---|---|---|---|
| 2007/0272564 A1* | 11/2007 | Huang | G01N 27/3273 205/792 |
| 2008/0302659 A1 | 12/2008 | Sheppard, Jr. et al. | |
| 2010/0025238 A1* | 2/2010 | Gottlieb | A61B 5/14532 204/401 |
| 2011/0048938 A1* | 3/2011 | Shah | A61B 5/14532 204/403.01 |
| 2014/0027312 A1* | 1/2014 | MacFie | G01N 27/3274 205/792 |
| 2016/0177931 A1 | 6/2016 | Shin et al. | |

FOREIGN PATENT DOCUMENTS

| | | |
|---|---|---|
| JP | 2009-145089 A | 7/2009 |
| KR | 10-2009-0023541 A | 3/2009 |
| KR | 10-2009-0118314 A | 11/2009 |
| WO | 2009-028920 A2 | 3/2009 |
| WO | 2009-139522 A1 | 11/2009 |
| WO | 2015/030466 A1 | 3/2015 |

* cited by examiner

GLUCOSE MEASUREMENT
(0,100,200,300,400mg/dl)

GLUCOSE MEASUREMENT
(0,100,200,300,400mg/dl)

GLUCOSE MEASUREMENT
(0,100,200,300,400mg/dl)

| CONCENTRATION (mg/dL) | AVERAGE (A) | STANDARD DEVIATION(A) | CV(%) |
|---|---|---|---|
| 0 | 0.00E+00 | 0.00E+00 | 0.00 |
| 100 | 1.27E-08 | 4.44E-09 | 35.05 |
| 200 | 2.30E-08 | 2.00E-09 | 8.71 |
| 300 | 2.79E-08 | 2.85E-09 | 10.22 |
| 400 | 2.95E-08 | 1.76E-09 | 5.97 |
| | | | 14.99 |

| CONCENTRATION (mg/dL) | AVERAGE (A) | STANDARD DEVIATION(A) | CV(%) |
|---|---|---|---|
| 0 | 0.00E+00 | 0.00E+00 | 0 |
| 100 | 1.17E-06 | 2.62E-08 | 2.25 |
| 200 | 2.39E-06 | 4.55E-08 | 1.90 |
| 300 | 3.70E-06 | 5.04E-08 | 1.36 |
| 400 | 5.01E-06 | 5.88E-08 | 1.17 |
|  |  |  | 1.67 |

BIO SENSOR AND SENSING METHOD THEREOF

CROSS-REFERENCE TO RELATED APPLICATION(S)

This application claims the benefit under 35 U.S.C. § 119(a) of a Korean patent application filed on Nov. 3, 2015 in the Korean Intellectual Property Office and assigned Serial number 10-2015-0154026, the entire disclosure of which is hereby incorporated by reference.

TECHNICAL FIELD

The present disclosure relates to a bio sensor and a sensing method thereof. More particularly, the present disclosure relates to a bio sensor and a sensing method thereof, for ensuring reproducibility in a continuous measurement.

BACKGROUND

Quantitative determination of one or more analytes in biological fluids is very useful for diagnosis and treatment of electrophysiological abnormalities. For example, it is necessary to periodically measure the amount of glucose (e.g., blood glucose) in blood in order to diagnose and prevent diabetes mellitus, a chronic, lifelong condition that affects a body's ability to use energy found in food.

An operation principle of a bio sensor for measuring one or more analytes in biological fluids is mainly based on an electrochemical method. An electrochemical bio sensor is a device for measuring the amount of a measurement target material via a method of detecting an electrochemical through an enzyme reaction with the measurement target material using an enzyme electrode formed by fixing an enzyme to an electrode.

However, when such an electrochemical bio sensor is continuously used, performance of the bio sensor is degraded for various external reasons. In particular, it is difficult to ensure reproducibility in continuous measurement as various interfering substances that are present in blood or intercellular fluid are adhered to an electrode of the sensor.

Typically, in order to prevent interfering substances from being adhered to an electrode, an electrode protective layer with micro pores is used, but there is a limitation in that the electrode protective layer is not capable of preventing the penetration of interfering substances with a smaller size than the analysis target material.

The above information is presented as background information only to assist with an understanding of the present disclosure. No determination has been made, and no assertion is made, as to whether any of the above might be applicable as prior art with regard to the present disclosure.

SUMMARY

Aspects of the present disclosure are to address at least the above-mentioned problems and/or disadvantages and to provide at least the advantages described below. Accordingly, an aspect of the present disclosure is to provide a bio sensor for ensuring reproducibility in continuous measurement and a sensing method of the bio sensor.

In accordance with an aspect of the present disclosure, a bio sensor is provided. The bio sensor includes an electrode array including an enzyme electrode configured to measure a target material, a power driver configured to provide a voltage to the electrode array, and a processor configured to control the power driver to alternately provide a negative voltage and a positive voltage to the electrode array, and to control the power driver to provide a measurement voltage for measuring the target material to the electrode array after the alternating voltage is provided.

The processor may further be configured to control the power driver to provide the measurement voltage to the electrode array when a preset time period elapses after the alternating voltage is provided.

The preset time period may be 30 to 60 seconds.

The processor may further be configured to control the power driver to initially provide a negative voltage when the alternating voltage is provided.

The processor may further be configured to control the power driver to provide the alternating voltage to the electrode array in the form of a pulse.

The processor may further be configured to control the power driver to provide the alternating voltage to the electrode array in a continuous form.

The processor may further be configured to control the power driver to provide the alternating voltage in the range which is greater than 0 V and equal to or less than 1.5 V.

The enzyme electrode may include an enzyme for oxidizing glucose.

The processor may further be configured to measure the target material based on current flowing in the electrode array in response to the measurement voltage being provided to the electrode array.

The bio sensor may further include a display configured to display a measurement result of the target material.

In accordance with another aspect of the present disclosure, a method of sensing for a bio sensor comprising an electrode array, the electrode array including an enzyme electrode configured to measure a target material, is provided. The method includes alternately providing a negative voltage and a positive voltage to the electrode array, and providing a measurement voltage for measuring the target material to the electrode array after the alternating voltage is provided.

The providing of the measurement voltage may include providing the measurement voltage when a preset time period elapses after the alternating voltage is provided.

The preset time period may be 30 to 60 seconds.

The alternately providing of the negative voltage and the positive voltage may include initially providing the negative voltage to the electrode array.

The alternately providing of the negative voltage and the positive voltage may include alternately providing the negative voltage and the positive voltage in a form of a pulse.

The alternately providing of the negative voltage and the positive voltage may include alternately providing the negative voltage and the positive voltage in a continuous form.

The alternately providing of the negative voltage and the positive voltage may include alternately providing the negative voltage and the positive voltage in a range which is greater than 0 V and equal to or less than 1.5 V.

The enzyme electrode may include an enzyme for oxidizing glucose.

The method may further include measuring the target material based on current flowing in the electrode array in response to the measurement voltage being provided to the electrode array.

The method may further include displaying a measurement result of the target material.

Other aspects, advantages, and salient features of the disclosure will become apparent to those skilled in the art from the following detailed description, which, taken in conjunction with the annexed drawings, discloses various embodiments of the present disclosure.

BRIEF DESCRIPTION OF THE DRAWINGS

The above and other aspects, features, and advantages of certain embodiments of the present disclosure will be more apparent from the following description taken in conjunction with the accompanying drawings, in which.

Throughout the drawings, it should be noted that like reference numbers are used to depict the same or similar elements, features, and structures.

DETAILED DESCRIPTION

Figure 1:
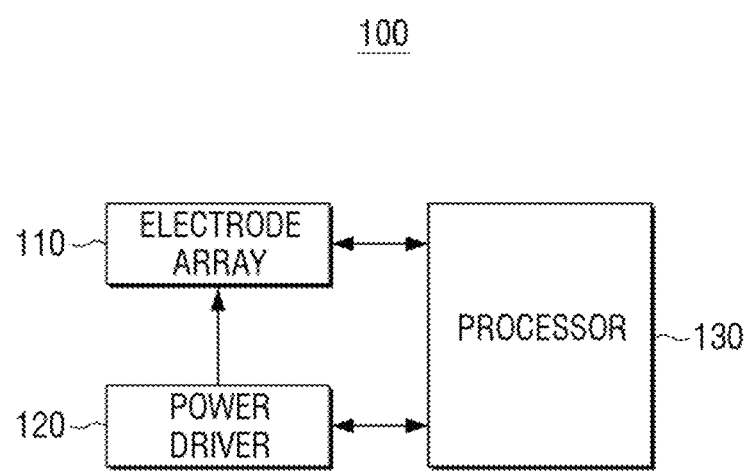
FIG. 1 is a diagram illustrating a structure of a bio sensor according to an embodiment of the present disclosure.

The following description with reference to the accompanying drawings is provided to assist in a comprehensive understanding of various embodiments of the present disclosure as defined by the claims and their equivalents. It includes various specific details to assist in that understanding but these are to be regarded as merely exemplary. Accordingly, those of ordinary skill in the art will recognize that various changes and modifications of the various embodiments described herein can be made without departing from the scope and spirit of the present disclosure. In addition, descriptions of well-known functions and constructions may be omitted for clarity and conciseness.

The terms and words used in the following description and claims are not limited to the bibliographical meanings, but, are merely used by the inventor to enable a clear and consistent understanding of the present disclosure. Accordingly, it should be apparent to those skilled in the art that the following description of various embodiments of the present disclosure is provided for illustration purpose only and not for the purpose of limiting the present disclosure as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

With respect to the terms used in an example embodiment of the disclosure, general terms currently and widely used are selected in view of function with respect to the disclosure. However, the terms may vary according to an intention of a technician practicing in the pertinent art, an advent of new technology, etc. In specific cases, terms may be chosen arbitrarily, and in this case, definitions thereof will be described in the description of the corresponding disclosure. Accordingly, the terms used in the description should not necessarily be construed as simple names of the terms, but be defined based on meanings of the terms and overall contents of the present disclosure.

The example embodiments may vary, and may be provided in different example embodiments. Various example embodiments will be described with reference to accompanying drawings. However, this does not necessarily limit the scope of the example embodiments to a specific embodiment form. Instead, modifications, equivalents and replacements included in the disclosed concept and technical scope of this description may be employed. While describing example embodiments, if it is determined that the description regarding a known technology obscures the gist of the present disclosure, a detailed description may be omitted.

The term such as "first" "second", and so on may be used to explain a variety of elements, but the elements should not be limited thereto. The terms are used to distinguish one entity from another entity, without necessarily implying any actual relationship or order between such entities.

The terms, "include," "comprise," "is configured to," etc. of the description are used to indicate the existence of features, numbers, operations, elements, parts or combination thereof, and do not exclude the possibilities of combination or addition of one or more features, numbers, operations, elements, parts or combination thereof.

In an example embodiment, 'a module' or 'a unit' performs at least one function or operation, and may be realized as hardware, software, or combination thereof. Further, except the "modules" or "units" that have to be implemented by certain hardware, a plurality of "modules" or a plurality of "units" may be integrated into at least one module and realized as at least one processor (not illustrated).

In an embodiment, in the case where a part is "connected" to another part, the case also includes a case where the part is "electrically connected" to the other part with another element interposed therebetween.

Hereinafter, the example embodiments will be described in greater detail in a manner that will be understood by one of ordinary skill in the art. The example embodiments may be implemented by various forms, and is not limited to the example embodiments described herein. Further, those that are irrelevant with the description are omitted so as to describe various embodiments more clearly, and similar drawing reference numerals are used for the similar elements throughout the description.

Hereinafter, the present disclosure will be described in detail with reference to the accompanying drawings.

FIG. 1 is a diagram illustrating a structure of a bio sensor 100 according to an embodiment of the present disclosure.

Referring to FIG. 1, the bio sensor 100 may include an electrode array 110, a power driver 120, and a processor 130.

The bio sensor 100 may be a device for measuring a target material via an electrochemical method using a biological substance, for example, an enzyme with a specific recognition capability with respect to an analysis material. The term "bio sensor" has been used thus far but various terms of a sensor, such as a measuring device, a measuring instrument, and the like may be used.

In detail, an electron transfer may occur according to biochemical oxidation and reduction reactions at an electrode surface of the bio sensor 100 and current may be generated according to the electron transfer may be monitored in order to measure a concentration of a target material in a sample.

The electrode array 110 may include a pair of electrodes and measure the current flowing between the pair of electrodes to quantify a target material.

In detail, the electrode array 110 may include a working electrode and a counter electrode (or a counter or counter/reference electrode). According to another embodiment of the present disclosure, the electrode array 110 may include a working electrode, a counter electrode, and a separated reference electrode.

Figure 2A:
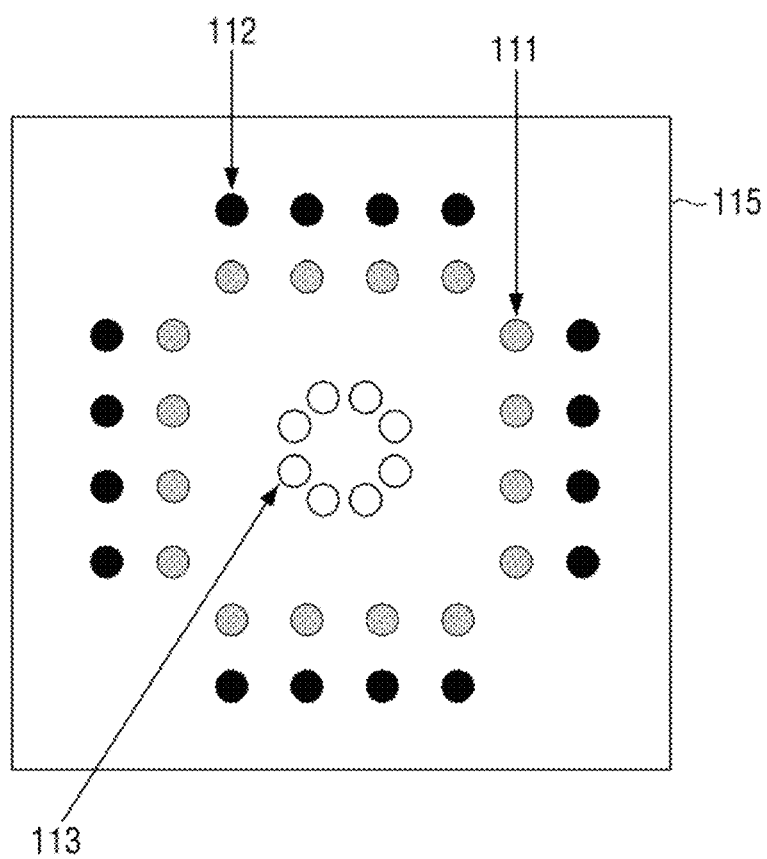
FIGS. 2A and 2B are diagrams illustrating an electrode array of a bio sensor according to various embodiments of the present disclosure.

FIG. 2A is a diagram illustrating the electrode array 110 according to an embodiment of the present disclosure.

Referring to FIG. 2A, FIG. 2A illustrates the electrode array 110 viewed from the above. The electrode array 110 may include a plurality of working electrodes (e.g., enzyme electrodes) 111, a plurality of counter electrodes 112, a plurality of reference electrodes 113, and a support 115 for supporting each electrode. Arrangement of the electrodes illustrated in FIG. 2A is a merely an example and the present disclosure is not limited to the arrangement.

Figure 2B:
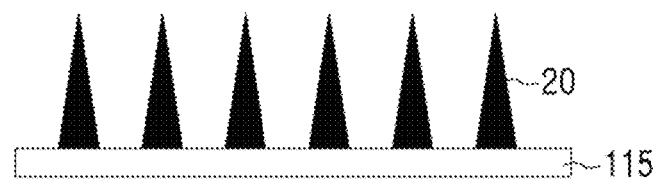

FIG. 2B is a diagram illustrating the electrode array 110 viewed from a lateral according to an embodiment of the present disclosure.

Referring to FIG. 2B, the electrode array 110 may include a plurality of electrodes 20 arranged on the support 115 and the plurality of electrodes 20 may include a working electrode, a counter electrode, and a reference electrode.

Alternatively, the plurality of electrodes 20 may include a working electrode and a counter electrode. In addition, a plurality of electrodes may be used as described with reference to FIG. 2A.

The plurality of electrodes 20 may be shaped like a needle so as to be insertable into the skin of a user. In this case, the plurality of electrodes 20 shaped like a needle may each have a length such that each electrode passes through the stratum corneum of the skin, but is not inserted into the hypodermis of the skin in which blood vessels are distributed. Accordingly, the length of the plurality of electrodes 20 may be selected in the range of 100 μm to 5 mm. In addition, the density, shape, and aspect ratio of the plurality of electrodes 20 may be appropriately selected in consideration of processibility, mechanical strength, and so on.

Hereinafter, various electrodes included in the electrode array 110 will be described in detail.

A working electrode is fixed with an enzyme and, thus, it may also be referred to as an enzyme electrode. In the working electrode, an enzyme and an electron transfer medium may be fixed and the enzyme of the working electrode may be determined according to a measurement target material. For example, when glucose is a measurement target material, the working electrode may include an enzyme for oxidizing glucose.

For example, glucose, glutamate, cholesterol, lactate, ascorbic acid, alcohol, bilirubin may be measured by using a glucose oxidation enzyme (e.g., glucose oxidase (GOx)), a glucose dehydro enzyme (e.g., glucose dehydrogenase (GDH)), a glutamate oxidation enzyme (e.g., glutamate oxidase), a glutamate dehydro enzyme (e.g., glutamate dehydrogenase), a cholesterol oxidation enzyme, a cholesterol esterified enzyme, a lactate oxidation enzyme, an ascorbic acid oxidation enzyme, an alcohol oxidation enzyme, an alcohol dehydro enzyme (e.g., alcohol dehydrogenase (ADH)), a bilirubin oxidation enzyme, and the like. As necessary, two or more types of enzymes may be fixed to the working electrode.

For example, when a target material is glucose, and when glucose and a glucose oxidation enzyme fixed to the working electrode react with each other, gluconic acid is oxidized. In addition, an electric current that is generated according to an electron transfer that occurs when oxygen or an oxidized medium is changed to hydrogen peroxide or a reduced medium during the oxidation of glucose and re-oxidized to restore to an originally oxidized form may be measured to quantify the glucose in a sample.

Examples of an electron transfer medium material may include ferrocene, ferrocene derivatives, quinine, quinine derivatives, transition metal-containing organic and inorganic substances (e.g., hexaamineruthenium, osmium-containing polymer, potassium ferricyanide, etc., organic conducting salt, or viologen).

The counter electrode has an opposite polarity to the working electrode and functions as a current path between the electrodes and, thus, the counter electrode may be formed of an electrode material with high electro conductivity.

The working electrode and the counter electrode may be manufactured via, for example, screen printing using a carbon paste.

In addition, the working electrode and the counter electrode may be formed of, for example, a precious metal such as platinum (Pt), gold (Au), and silver (Ag) or alloy including the same. In particular, platinum (Pt) and silver (Ag) are hygienically advantageous due to having a germicidial effect according to a catalytic reaction.

The reference electrode permits a constant voltage to be applied to the working electrode and prevents the current from flowing toward the working electrode due to high impedance. The reference electrode may be, for example, be a standard hydrogen electrode (SHE), a calomel (Hg/$Hg_2Cl_2$) electrode, or a silver-silver chloride (Ag/AgCl) electrode. The reference electrode has a comparatively constant potential difference and thus, a constant electrode voltage may be applied to the reference electrode. For example, the reference electrode may be manufactured via screen printing using Ag/AgCl ink.

The power driver 120 may be a component for providing a voltage to the electrode array 110.

The power driver 120 may provide any one type of voltage among a direct current (DC) voltage, an alternating current (AC) voltage, and a voltage formed via an overlap between a DC voltage and an AC voltage to the electrode array 110.

The processor 130 may be a component for controlling an overall operation of the bio sensor 100.

In particular, the processor 130 may control the power driver 120 to provide a voltage to the electrode array 110.

In detail, the processor 130 may control the power driver 120 to provide a measurement voltage for measuring a target material to the electrode array 110.

Here, the measurement voltage may be a voltage value appropriate to oxidize only a target material and may prevent other materials in a sample from being oxidized and participating in a current component. For example, when the target material is glucose, the processor 130 may control the power driver 120 to provide a measurement voltage in the range of 0 to 1 V.

In particular, the processor 130 may control the power driver 120 to provide an initialization voltage (or reset voltage) in order to restore an enzyme electrode (working electrode) to an initial state of the electrode array 110 before the measurement voltage is applied. The initialization voltage may be provided by alternately providing a negative voltage and a positive voltage.

The restoration of the enzyme electrode to an initial state may include removing interfering substances that are adhered to a surface of an enzyme electrode and interfere with measurement of a target material.

For example, when the bio sensor 100 is used to measure blood glucose, interfering substances that may be present in blood (e.g., ions such as $Cl^-$, $Ca^{2+}$, and $Mg^{2+}$), after the measurement is performed, the interfering substances may be adhered to an enzyme electrode. As such, when subsequent measurement is performed while interfering substances are adhered to the enzyme electrode, a measurement value that is different from the actual blood glucose contents may be obtained. Accordingly, in order to remove the interfering substances, the processor 130 may control the power driver 120 to alternately provide a negative voltage and a positive voltage to the electrode array 110 before the measurement voltage is applied. This action will detach the interfering substances from the enzyme electrode.

The restoration of the enzyme electrode to an initial state may include restoring an enzyme in a reduction state after the reaction to an oxidation state.

The enzyme becomes reduction state after reacting with a target material and then, the enzyme should be restored to an oxidation state by transmitting an electron to an electron transfer medium material. But a portion of the enzyme fixed to the enzyme electrode may not be restored to an oxidation state. Accordingly, in order to restore the enzyme to an oxidation state, the processor 130 may control the power driver 120 to provide alternately a negative voltage and a positive voltage before a measurement voltage is applied, which will be described with reference to FIG. 3.

Figure 3:
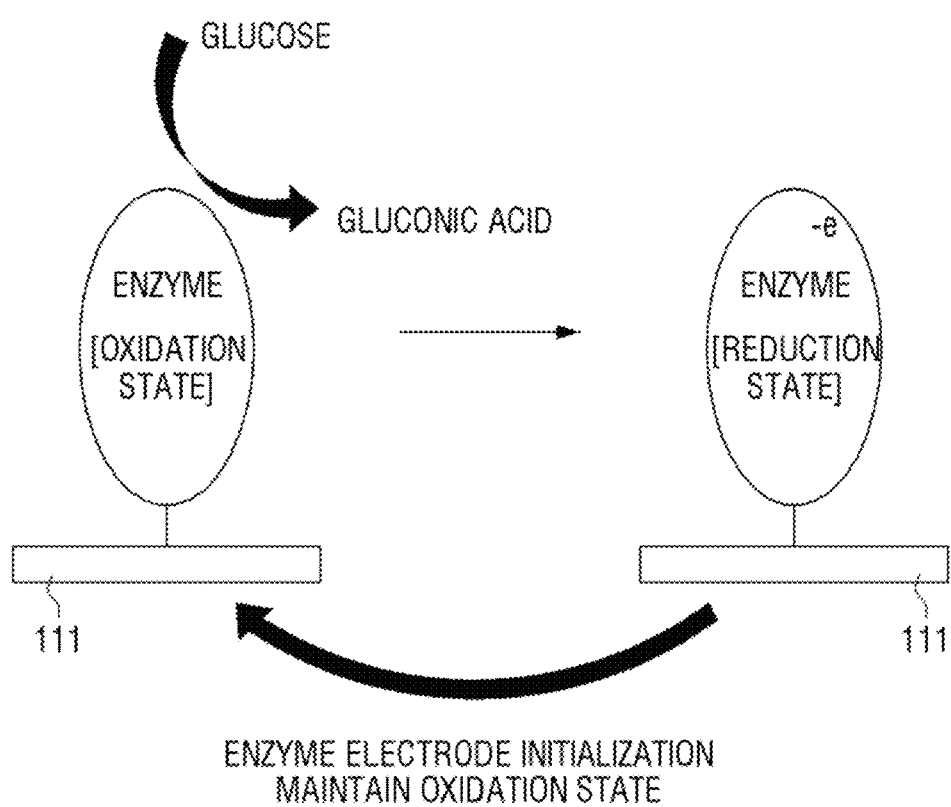
FIG. 3 is a diagram illustrating various states of an enzyme electrode according to an operation of a bio sensor according to an embodiment of the present disclosure.

FIG. 3 is a diagram illustrating various states of an enzyme electrode 111 before and after reaction with glucose when a measurement target material is glucose according to an embodiment of the present disclosure.

Referring to FIG. 3, an enzyme may be fixed to the enzyme electrode 111 of a sensor array 110. The enzyme in an oxidation state may oxidize glucose to gluconic acid and enter a reduction state. In addition, the enzyme in a reduction state may be oxidized and electrons may be moved to the enzyme electrode 111 and thus, current may be generated between the enzyme electrode 111 and a counter electrode (not shown) and the generated current may be measured to quantify glucose in a sample.

However, since all enzymes of the enzyme electrode 111 may not be capable of being restored to an oxidation state, the amount of the enzymes that may react with glucose is gradually reduced as the bio sensor 100 is repeatedly used and, thus, performance may be degraded. In particular, this issue may be serious in the case in where the bio sensor 100 is a continuous measurement type.

Accordingly, in order to restore the enzyme in a reduction state of the enzyme electrode to an oxidation state. That is, in order to initialize an enzyme electrode, the power driver 120 may alternately provide a negative voltage and a positive voltage to the electrode array 110 before a measurement voltage is applied.

In this case, the processor 130 may control the power driver 120 to provide an alternate voltage one or more times.

The processor 130 may control the power driver 120 to initially provide a negative voltage when providing an alternate voltage. That is, a negative voltage may first be provided and a positive voltage may lastly be provided before a measurement voltage is applied so as to restore an enzyme to a reduction state.

However, various embodiments of the present disclosure are not limited to the aforementioned order and thus, a positive voltage may first be provided and a negative voltage may be provided and then, a positive voltage may lastly be provided. When a positive voltage is first provided, negative ions from the interfering substances will further approach an enzyme electrode and are more largely affected by a subsequently applied negative voltage and thus, the interfering substances may be further moved to be far away from the enzyme electrode.

The alternately provided voltage may have various forms. According to an embodiment of the present disclosure, the processor 130 may control the power driver 120 to provide an alternate voltage to the electrode array 110 in the form of a pulse. According to another embodiment of the present disclosure, the processor 130 may control the power driver 120 to provide an alternate voltage to the electrode array 110 in a continuous form. The continuous form of voltage may be provided via cyclic voltammetry.

When the bio sensor 100 contacts a user's body during use (e.g., as in an implantable sensor type), if an excessively large voltage is provided, the voltage may adversely affect a user and thus, the positive voltage and the negative voltage that are alternately provided may be provided with a predetermined amplitude or less. For example, the amplitude of an alternately provided voltage may be set to 1.5 V or less.

For example, a voltage of −0.6 V and a voltage of +0.9 V may be alternately provided to the electrode array 110 in the form of a pulse. In this case, the amplitude of a pulse type voltage may be varied whenever the voltage is provided.

The alternately provided voltages may be provided in a different range from a range of a measurement voltage for oxidizing a target material.

In addition, the processor 130 may control the power driver 120 to provide a measurement voltage after an alternate voltage is provided to the electrode array 110 and then a preset time period elapses, as described above. That is, a voltage may not be provided to the electrode array 110 during a preset time period. This is because an enzyme electrode needs to be stabilized after the alternate voltage is provided. For example, the stabilizing time may be set to 30 to 60 seconds.

When a measurement voltage is provided to the electrode array 110, the processor 130 may measure a concentration of a target material based on current flowing in the electrode array 110.

In detail, the processor 130 may detect the current flowing in the electrode array 110 as a generating signal in response to the applied measurement voltage and perform a calculation using the generating signal so as to calculate a concentration of the target material.

According to an embodiment of the present disclosure, the processor 130 may include an analog digital converter (ADC), a calculator, and a memory. A current value may be input through the ADC and converted into a digital value. The calculator may output a concentration value of the target material using a digital current value output from the ADC. In addition, the calculated concentration value may be stored in the memory.

Current may be generated in response to an alternate voltage provided in order to initialize the enzyme electrode but the processor 130 may not use the current as a reference of measurement of the target material. That is, the current generated during initialization of the enzyme electrode may not be considered for measurement of the target material.

In order to reuse the bio sensor 100 after a measurement is completely performed, alternate initialization voltages of a negative voltage and a positive voltage, for initializing the enzyme electrode of the bio sensor 100, may be provided again.

In this case, according to an embodiment of the present disclosure, the processor 130 may control the power driver 120 to provide the alternate voltages of a negative voltage and a positive voltage with larger amplitude than an alternate voltage of a negative voltage and a positive voltage, which have been provided before. This is because that the amplitude of the initialization voltage is increased to more effectively prevent the reproducibility of the bio sensor 100 from being lowered due to continuous use since a degree of lowering the reproducibility of the enzyme electrode is increased as a use number of times of the bio sensor 100 is increased.

According to an embodiment of the present disclosure, the bio sensor 100 may include a display for displaying a measurement result. According to another embodiment of the present disclosure, the bio sensor 100 may include a communication interface for transmitting a measurement result to an external device. In this case, the external device may be a smartphone or the like and a user may check the measurement result through a smartphone or the like. In addition, the bio sensor 100 may be charged or powered by the external device (e.g., via a universal serial bus (USB) connection).

According to the aforementioned embodiments of the present disclosure, a negative voltage and a negative voltage may alternately be applied to restore an enzyme electrode to an initial state prior to measurement, thereby enhancing the reproducibility of the bio sensor 100 in continuous measurement.

Hereinafter, experimental results obtained via continuous measurement of glucose in a sample according to a comparative example and an embodiment of the present disclosure will be compared and described.

Figure 4:
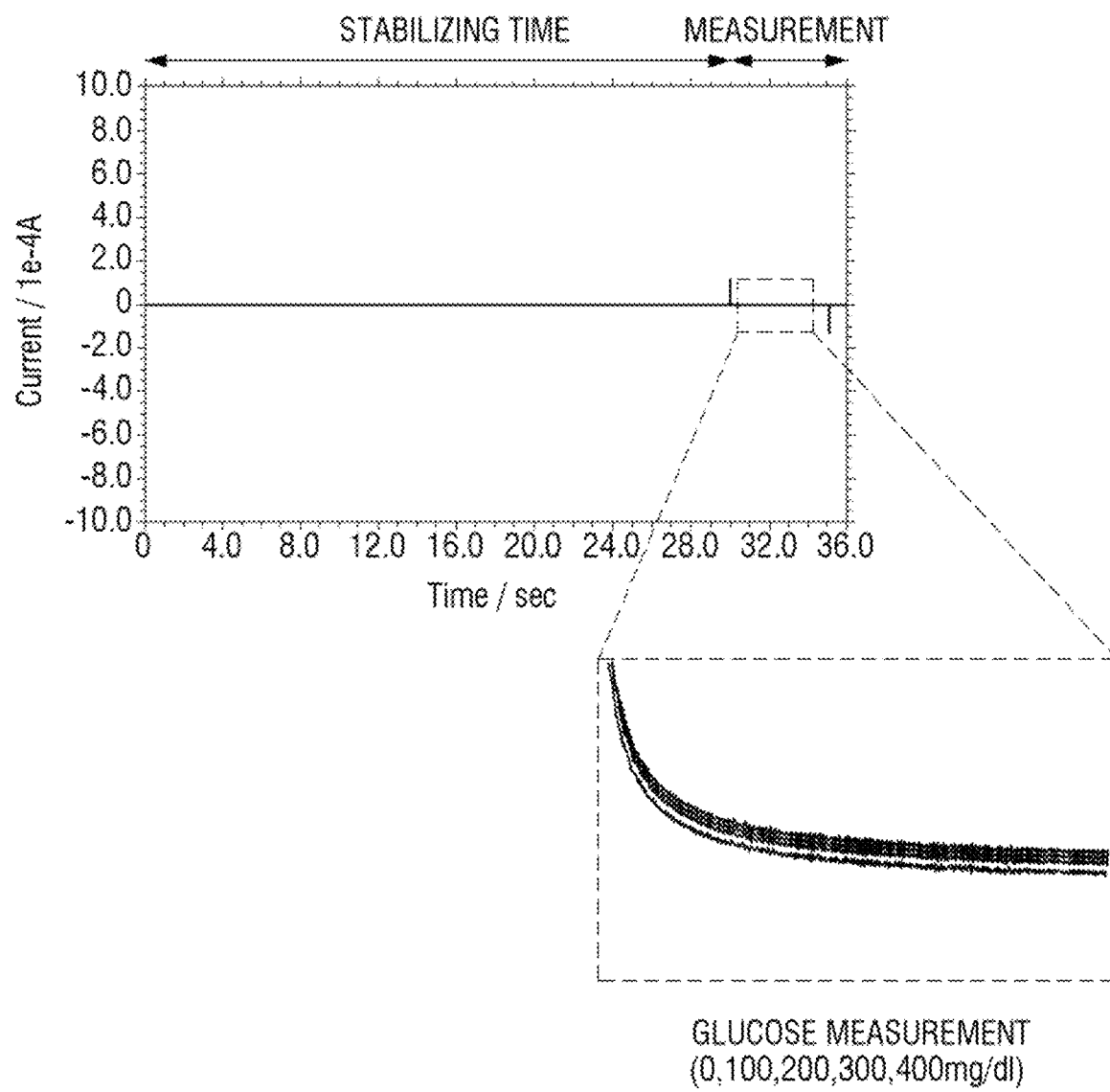
FIG. 4 is a diagram illustrating a measurement result using a bio sensor according to a comparative example, according to an embodiment of the present disclosure.

FIG. 4 illustrates a result of continuous measurement of current variation according to time using a bio sensor as a concentration of glucose in a sample is increased by 100 mg/dl at a stabilization time interval, as a comparative example according to an embodiment of the present disclosure. A voltage is not applied in the stabilization time interval and a measurement voltage is applied in a measurement period.

Referring to FIG. 4, with reference to a current variation curve according to each concentration in a measurement period of FIG. 4, when a concentration of glucose is 0 mg/dl, when a concentration of glucose is 100 mg/dl, when a concentration of glucose is 200 mg/dl, when a concentration of glucose is 300 mg/dl, and when a concentration of glucose is 400 mg/dl, current variation curves are not differentiated. This indicates that a bio sensor is degraded according to continuous measurement.

Figure 5:
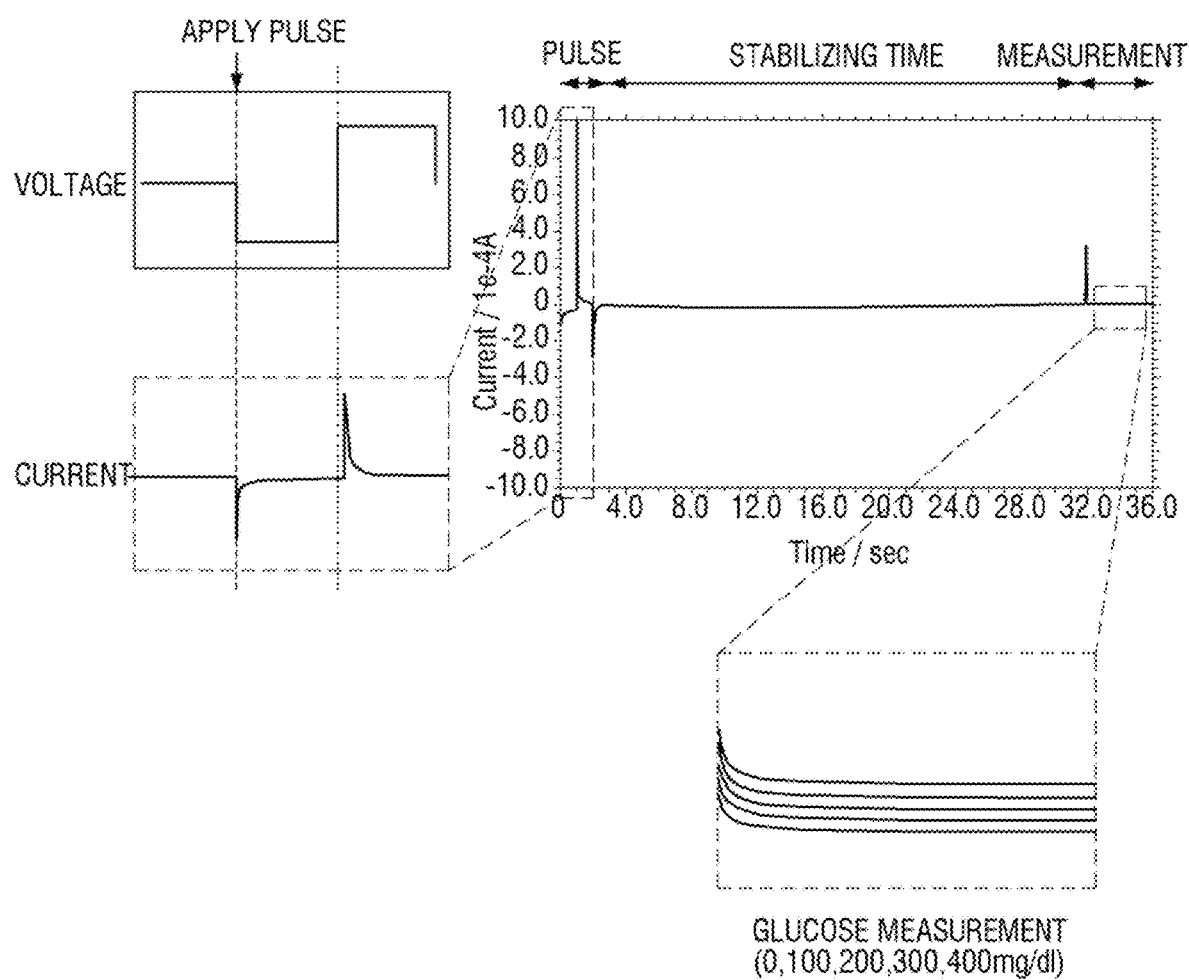
FIG. 5 is a diagram illustrating a measurement result using a bio sensor according to an embodiment of the present disclosure.

FIG. 5 illustrates a result of continuous measurement of current variation according to time, using a bio sensor, as a concentration of glucose is increased by 100 mg/dl in the same way as the comparative example of FIG. 4 according to an embodiment of the present disclosure. However, unlike in the comparative example of FIG. 4, a negative voltage pulse and a positive voltage pulse are applied prior to measurement.

Referring to FIG. 5, with reference to a current variation curve according to each concentration in a measurement period of FIG. 5, when a concentration of glucose is 0 mg/dl, when a concentration of glucose is 100 mg/dl, when a concentration of glucose is 200 mg/dl, when a concentration of glucose is 300 mg/dl, and when a concentration of glucose is 400 mg/dl, current variation curves are differentiated. This indicates that a bio sensor is not degraded according to continuous measurement. That is, compared with the comparative example of FIG. 4, the reproducibility of a bio sensor may be improved.

Figure 6:
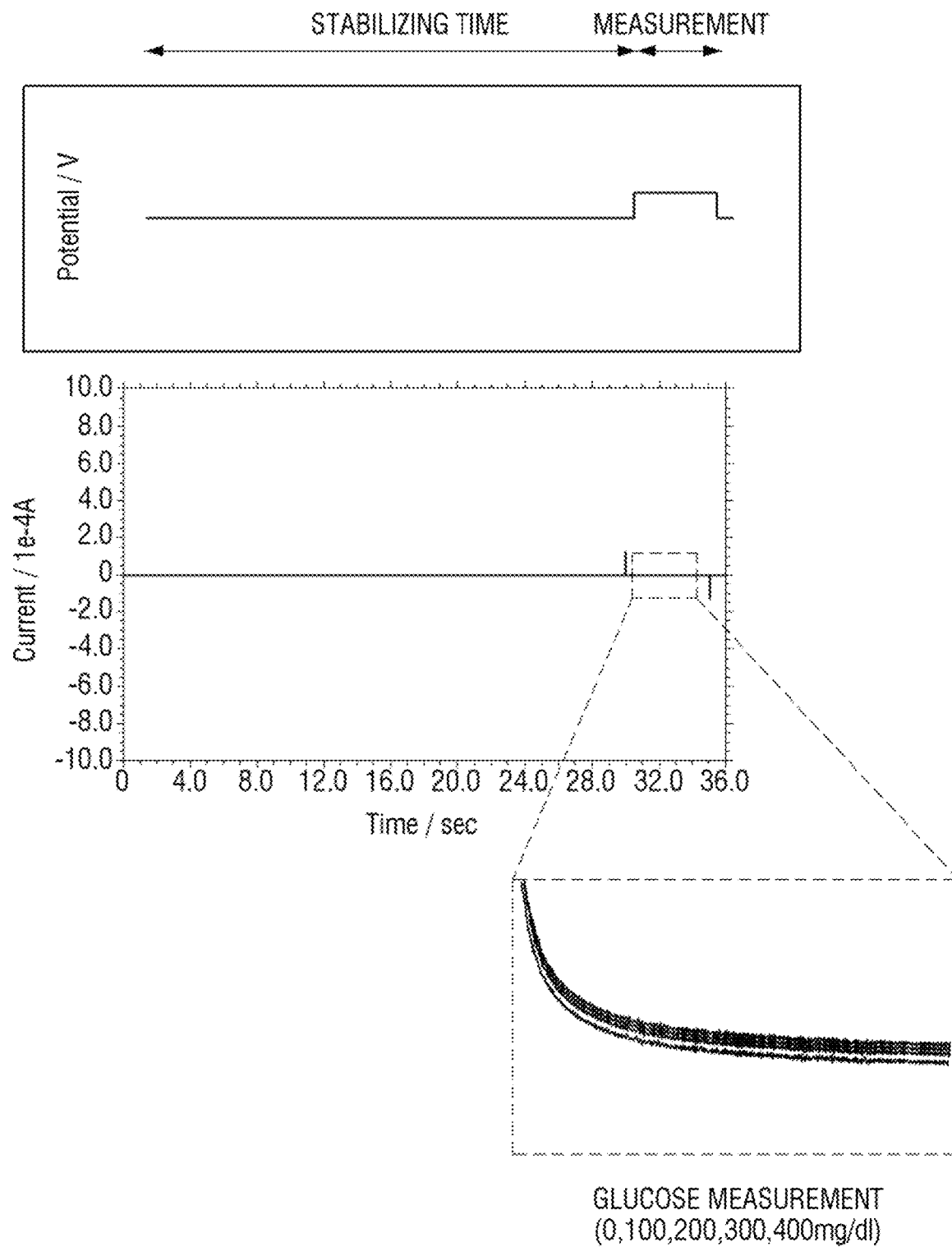
FIG. 6 is a diagram illustrating providing of a voltage of a bio sensor according to a comparative example, according to an embodiment of the present disclosure.
Figure 7:
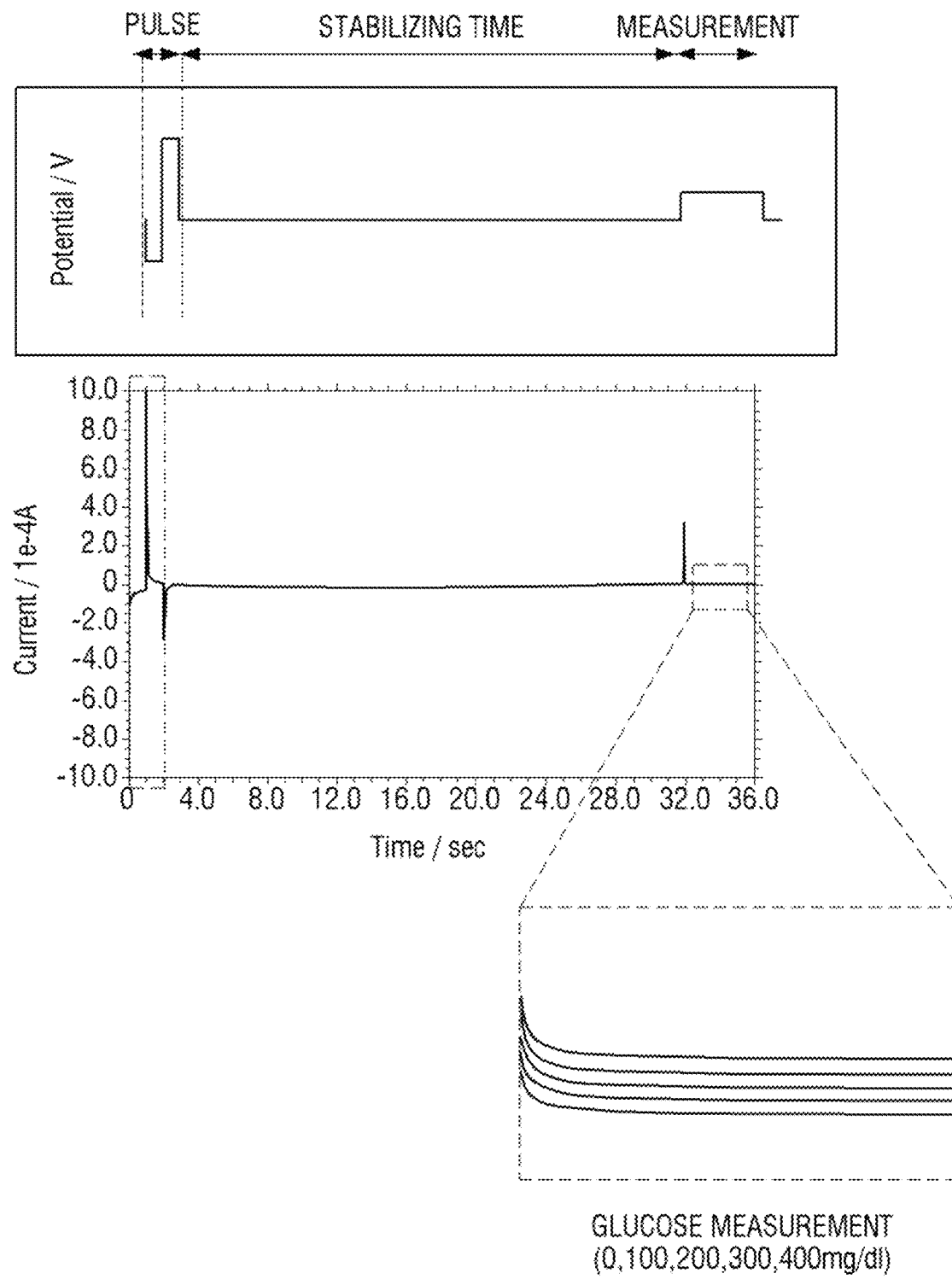
FIG. 7 is a diagram illustrating providing of a voltage of a bio sensor according to an embodiment of the present disclosure.

FIGS. 6 and 7 illustrate measurement results of a concentration of glucose in a sample according to a comparative example according to various embodiments of the present disclosure. According to an embodiment of the present disclosure, when alternate pulse voltages of a negative voltage and a positive voltage are applied prior to an application of a measurement voltage, the reproducibility of a bio sensor is enhanced.

Referring to FIG. 6, a voltage is not applied to an enzyme electrode of a bio sensor during a stabilization time interval and a measurement voltage is applied during a measurement period. In this case, the measurement voltage may be constantly applied in the range of 0.4 to 0.7 V.

With reference to current variation according to time in a measurement period of FIG. 6, although a concentration of glucose in a sample is increased to 0, 100, 200, 300, and 400 mg/dl, current curves are not obviously differentiated.

Referring to FIG. 7, unlike an experimental condition of FIG. 6, after a negative pulse and a positive voltage pulse are applied and then a stabilization time period elapses, a measurement voltage is applied. In this case, the amplitude of a negative voltage pulse and a positive voltage pulse, that is, an absolute value may be set in the range between 0 and 1.5 V. In detail, in the experiment of FIG. 7, the negative voltage pulse may be −0.6 V and the positive voltage pulse may be +0.9 V. Alternate voltages of the negative voltage and the positive voltage may be applied for a time duration in the range of 1 to 10 seconds. In detail, in the experiment of FIG. 7, a pulse voltage is applied for two seconds. In addition, the measurement voltage is applied under the same condition as in the comparative example of FIG. 6.

With reference to current variation according to time in the measurement period of FIG. 7, as a concentration of glucose in a sample is increased to 0, 100, 200, 300, and 400 mg/dl, current variation curves are obviously differentiated. That is, compared with the comparative example of FIG. 6 and the embodiment of FIG. 7, the reproducibility of a sensor in continuous measurement is also highly accurate.

FIGS. 8, 9, 10, and 11 illustrate analysis results of linearity and accuracy of measurement results according to a comparative example and various embodiments of the present disclosure. Here, an analysis target material is glucose in a sample.

Figure 8:
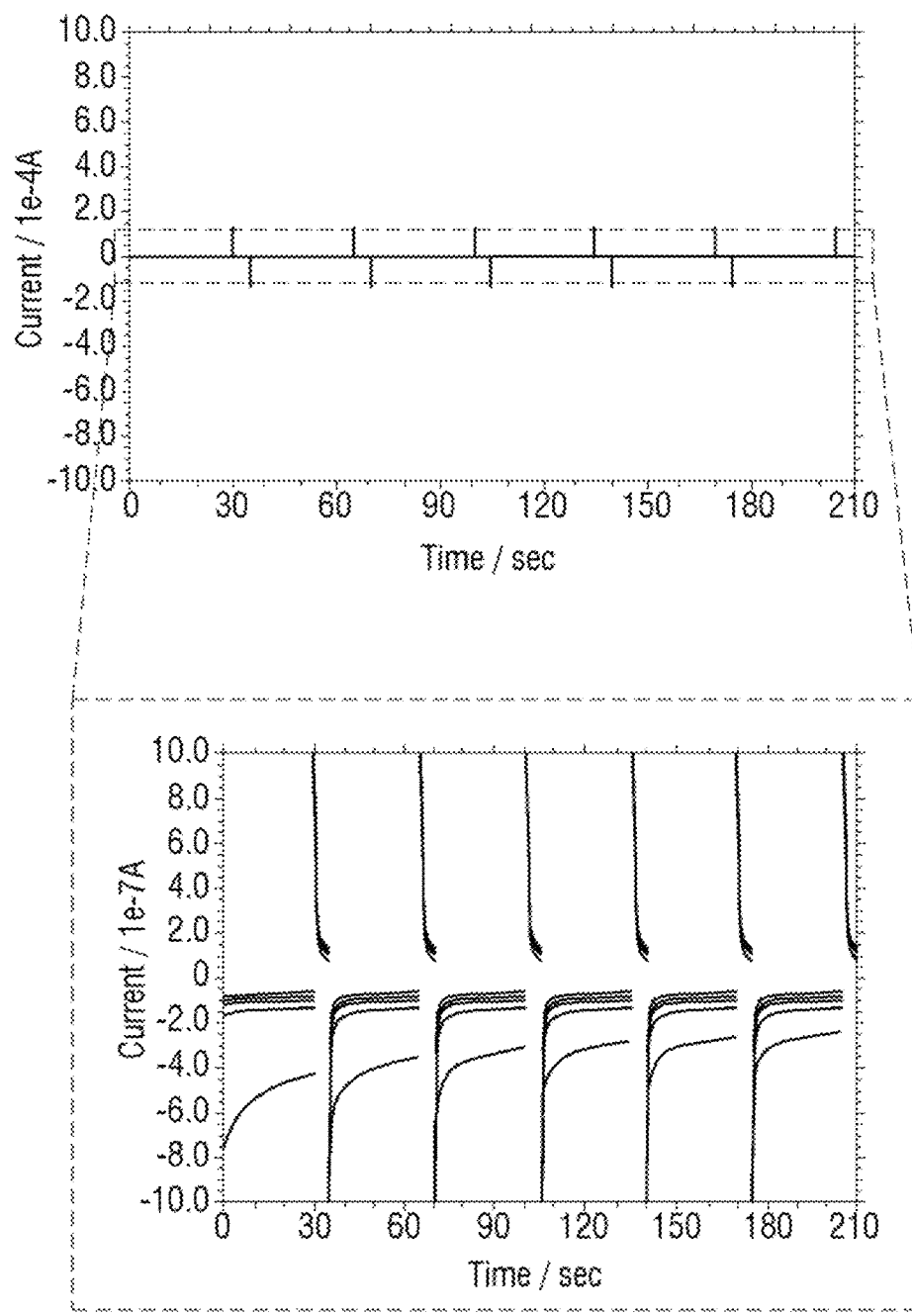
FIGS. 8 and 9 are diagrams illustrating experimental results of linearity and accuracy of a measurement result using a bio sensor according to a comparative example, according to various embodiments of the present disclosure.
Figure 9:
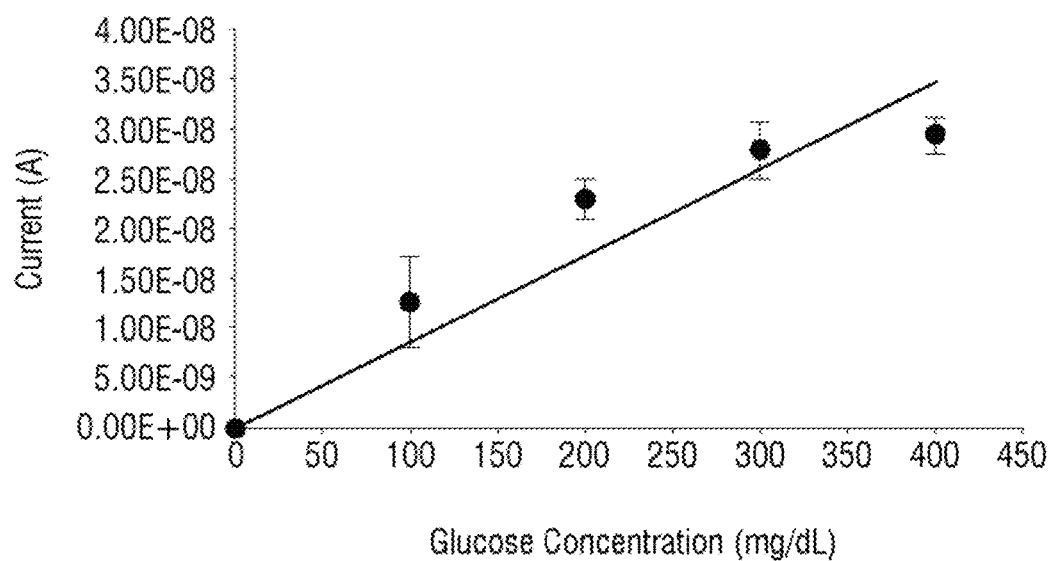

FIG. 8 illustrates a measurement result of current only in a stabilization time period according to a comparative example and FIG. 9 is a diagram formed by summarizing the result of FIG. 8.

Figure 10:
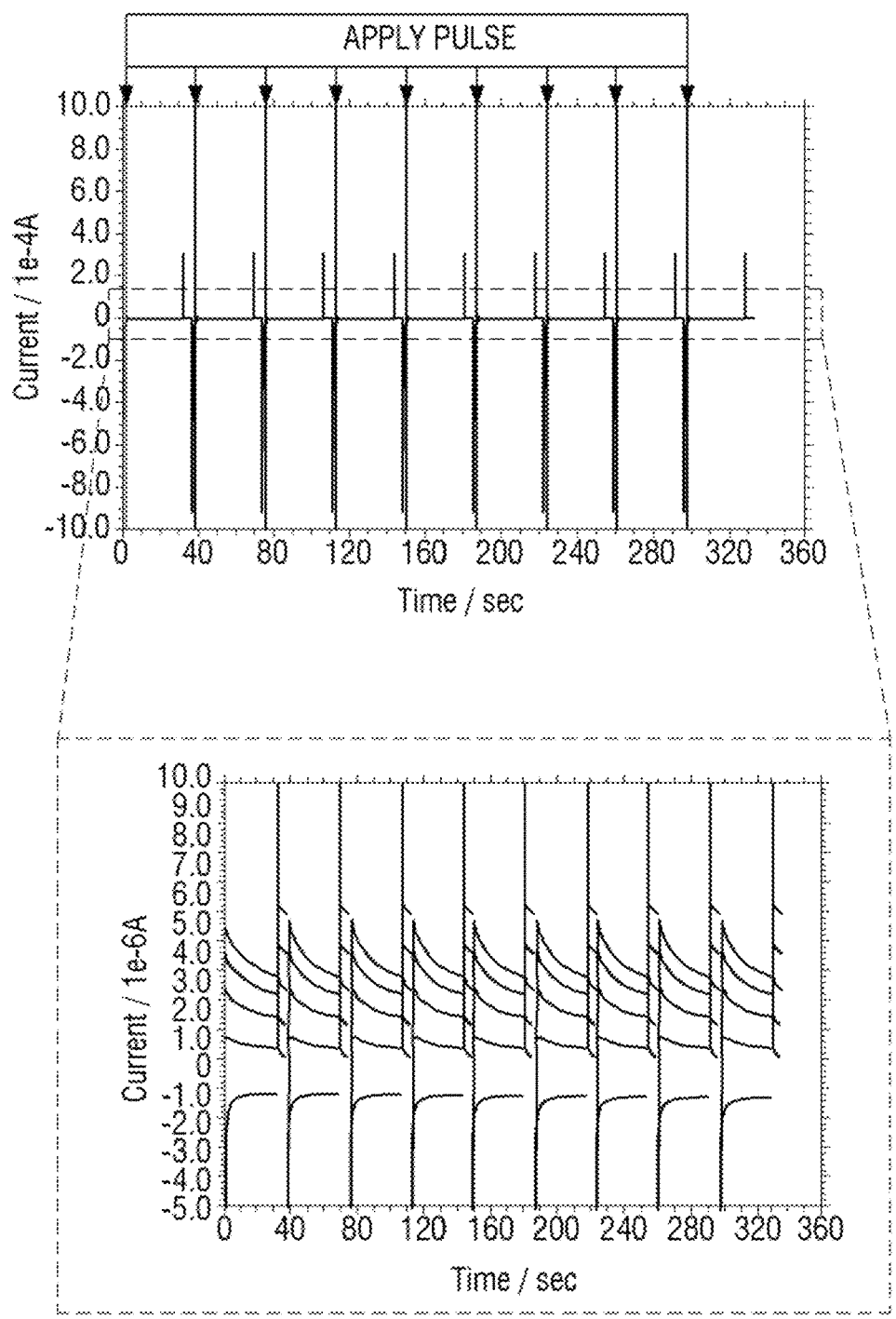
FIGS. 10 and 11 are diagrams illustrating experimental results of linearity and accuracy of a measurement result using a bio sensor according to various embodiments of the present disclosure.
Figure 11:
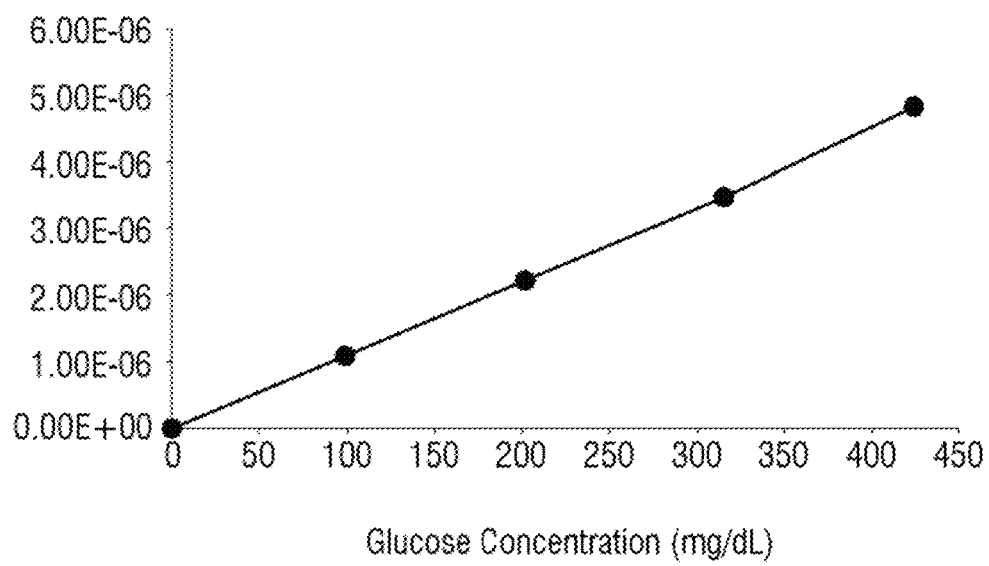

FIG. 10 illustrates a measurement result of current when a negative voltage pulse and a positive voltage pulse are alternately applied prior to measurement and then a stabilization time period elapses, according to an embodiment of the present disclosure, and FIG. 11 is a diagram formed by summarizing the result of FIG. 10.

In detail, FIGS. 8 and 10 illustrate amounts of current variation that is measured in the case of each concentration of glucose, that is, 0, 100, 200, 300, and 400 mg/dl according to a comparative example and an embodiment of the present disclosure. Referring to FIG. 9 formed by summarizing the measurement result of FIG. 8, R2 as a correlation coefficient of a blood glucose level for each concentration is 0.8695. On the other hand, as seen from FIG. 11 formed by summarizing the measurement result of FIG. 10 according to an embodiment of the present disclosure, R2 as a correlation coefficient of a blood glucose level for each concentration is 0.9991 and, thus, linearity is superior to the Comparative Example.

It may be seen that accuracy according to an embodiment of the present disclosure is highly accurate. In detail, with reference to FIG. 9 illustrating a result of a Comparative Example, an average value of percentage coefficient of variation (% CV) is 14.99. On the other hand, as seen from FIG. 11 illustrating a result of an embodiment of the present disclosure, an average value of percentage coefficient of variation is 1.67 and is much lower than in the Comparative Example. That is, accuracy in the case according to an embodiment of the present disclosure is far superior to the Comparative Example.

As seen from the aforementioned experimental results, when a negative voltage and a positive voltage are alternately applied before a measurement voltage for measuring a target material using a bio sensor is applied, high reproducibility and accuracy of measurement are obtained according to an embodiment of the present disclosure.

Figure 12:
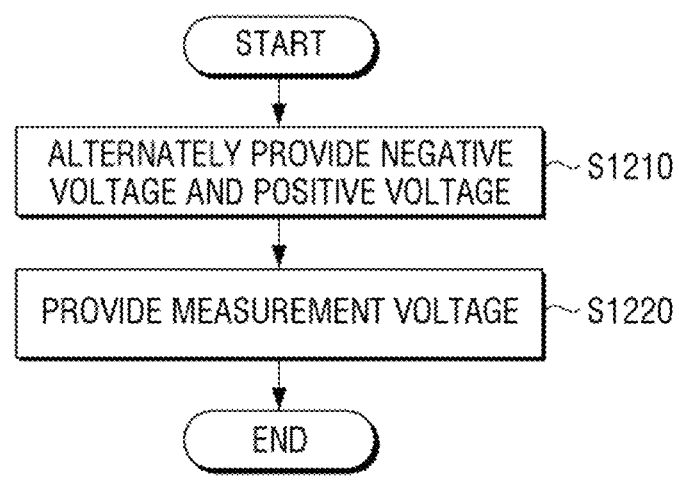
FIG. 12 is a flowchart illustrating a sensing method of a bio sensor according to an embodiment of the present disclosure.

FIG. 12 is a flowchart for explanation of a sensing method of a bio sensor including an electrode array including an enzyme electrode for measuring a target material according to an embodiment of the present disclosure.

Referring to FIG. 12, first, a negative voltage and a positive voltage are alternately provided to the electrode array at operation S1210.

In this case, according to an order of the alternate negative voltage and positive voltage, the negative voltage may first be provided and then the positive voltage may be provided. Alternatively, the positive voltage may first be provided, the negative voltage may be provided, and then the positive voltage may be provided.

The alternately applied voltages may be provided once or twice or more. For example, when the negative voltage is provided and then the positive voltage is provided to constitute one cycle, one cycle or two cycles or more may be provided to an electrode array.

A time period for applying alternate voltages may be appropriately adjusted according to time required for sensing. For example, the alternate voltages may be applied for 1 to 10 seconds.

The alternate voltage may be provided in various forms such as a pulse form and a continuous form and, thus, is not limited to a specific form.

After the alternate voltages are applied, a measurement voltage for measuring a target material may be applied to the electrode array at operation S1220.

In this case, after the alternate voltages are applied to the electrode array and then a stabilization time in which a voltage is not applied for a preset time period elapses, the measurement voltage is provided. During the stabilization time, an oxidation state of the enzyme electrode may be uniform. The stabilization time may be set to 30 seconds to 60 seconds but this is merely an example. Thus, the stabilization time may be appropriately set according to time required for sensing.

When the measurement voltage is applied, a target material may be measured based on current flowing a working electrode and a counter electrode of the electrode array in response to the measurement voltage. The measurement of the target material may include detection of presence of the target material or quantification of the target material.

The bio sensor may provide a measurement result to a user using various methods. According to an embodiment of the present disclosure, the bio sensor may include a display for displaying a measurement result. In this case, the display of the bio sensor may display measured values, and a guidance or warning message according to the measured values. In addition, the display of the bio sensor may display a description message indicating a measuring method.

A bio sensor according to another embodiment of the present disclosure may communicate with an external device and transmit a measurement result to the external device. In this case, a user may check a sensing result through the external device.

The various embodiments of the present disclosure described in the specification may be embodied using at least one of application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, and electrical units for performing other functions. In a software configuration, various embodiments described in the specification such as a procedure and a function may be embodied as separate software modules. Each of the software modules may perform one or more functions and operations described in the specification.

The aforementioned sensing method according to the various embodiments of the present disclosure may be embodied as a program including an algorithm to be executable by a computer, stored in a non-transitory readable medium, and provided. The non-transitory readable medium may be installed and used in various devices.

For example, a medium containing the aforementioned sensing method according to the various embodiments of the present disclosure may be installed in a typical bio sensor so as to perform the sensing method according to the various embodiments of the present disclosure.

The non-transitory computer readable medium is a medium that semi-permanently stores data and from which data is readable by a device, but not a medium that stores data for a short time, such as register, a cache, a memory, and the like. In detail, programs for executing the aforementioned various methods may be stored in the non-transitory computer readable medium, for example, a compact disc (CD), a digital versatile disc (DVD), a hard disc, a Blu-ray disc, a universal serial bus (USB), a memory card, a read only memory (ROM), and the like, and may be provided.

While the present disclosure has been shown and described with reference to various embodiments thereof, it will be understood by those skilled in the art that various changes in form and details may be made therein without departing from the spirit and scope of the present disclosure as defined by the appended claims and their equivalents.

What is claimed is:

1. A bio sensor comprising:
   an electrode array comprising:
   a plurality of enzyme electrodes configured to measure a target material, and a plurality of counter electrodes;
a power driver configured to provide a voltage to the electrode array; and
at least one processor configured to perform:
controlling the power driver to alternately provide a positive voltage and a negative voltage to the electrode array, and
controlling the power driver to provide a measurement voltage for measuring the target material to the electrode array when a preset stabilization time period elapses after the controlling of the power driver to alternately provide the positive voltage and the negative voltage in a continuous form, wherein the positive voltage and the negative voltage generate a current that is independent of measuring the target material,
wherein the controlling the power driver to alternately provide the positive voltage and the negative voltage comprises controlling the power driver to initially provide the positive voltage and then provide the negative voltage and lastly provide another positive voltage before the measurement voltage is provided.

2. The bio sensor as claimed in claim 1, wherein the preset stabilization time period is 30 to 60 seconds.

3. The bio sensor as claimed in claim 1, wherein the at least one processor is further configured to control the power driver to alternately provide the positive voltage and the negative voltage in a range which is greater than 0 V and equal to or less than 1.5 V.

4. The bio sensor as claimed in claim 1, wherein the plurality of enzyme electrodes comprises an enzyme for oxidizing glucose.

5. The bio sensor as claimed in claim 1, wherein the at least one processor is further configured to measure the target material based on current flowing in the electrode array in response to the measurement voltage being provided to the electrode array.

6. The bio sensor as claimed in claim 5, further comprising:
a display configured to display a measurement result of the target material.

7. A method of sensing for a bio sensor comprising an electrode array, the electrode array comprising: a plurality of enzyme electrodes configured to measure a target material and a plurality of counter electrodes, the method comprising:
alternately providing a positive voltage and a negative voltage to the electrode array; and
providing a measurement voltage for measuring the target material to the electrode array when a preset stabilization time period elapses after the alternately providing the positive voltage and the negative voltage in a continuous form, wherein the positive voltage and the negative voltage generate a current that is independent of measuring the target material,
wherein the alternately providing the positive voltage and the negative voltage comprises initially providing the positive voltage and then providing the negative voltage and lastly providing another positive voltage before the measurement voltage is provided.

8. The method as claimed in claim 7, wherein the preset stabilization time period is 30 to 60 seconds.

9. The method as claimed in claim 7, wherein the alternately providing of the positive voltage and the negative voltage comprises alternately providing the positive voltage and the negative voltage in a range which is greater than 0 V and equal to or less than 1.5 V.

10. The method as claimed in claim 7, wherein the plurality of enzyme electrodes comprises an enzyme for oxidizing glucose.

11. The method as claimed in claim 7, further comprising:
measuring the target material based on current flowing in the electrode array in response to the measurement voltage being provided to the electrode array.

12. The method as claimed in claim 11, further comprising:
displaying a measurement result of the target material.

13. The bio sensor as claimed in claim 1, wherein a magnitude of the measuring voltage is less than a magnitude of the alternately provided positive voltage and a magnitude of the alternately provided negative voltage.

* * * * *